United States Patent [19]

Simpson et al.

[11] Patent Number: 4,658,082
[45] Date of Patent: Apr. 14, 1987

[54] METHOD FOR PRODUCING INTACT PLANTS CONTAINING FOREIGN DNA

[75] Inventors: Robert B. Simpson, Danville; Linda J. Margossian, Albany, both of Calif.

[73] Assignee: Atlantic Richfield Company, Los Angeles, Calif.

[21] Appl. No.: 634,283

[22] Filed: Jul. 25, 1984

[51] Int. Cl.⁴ .................... C12N 15/00; C12N 1/00
[52] U.S. Cl. .................... 800/1; 435/172.3; 435/317; 47/58; 935/30; 935/56; 935/64; 935/67
[58] Field of Search .............. 435/172.3, 68, 317; 935/24, 30, 35, 56, 64, 67; 47/58; 800/1

[56] References Cited

FOREIGN PATENT DOCUMENTS 2327484  1/1984  Australia .................... 435/172.3
0120516 10/1984  European Pat. Off. ......... 435/172.3

OTHER PUBLICATIONS

Hooykaas-Van Slogteren et al, 1984, "Expression of Ti Plasmid Genes in monocotyledonous plants . . . ", *Nature*, vol. 311, pp. 763-764.

Plasmids of Medical Environmental & Commercial Importance, EMBO J., vol. 3, 3039-3041.

Ooms et al, 1981, "Crown Gall Plant Tumors of Abnormal Morphology Induced by *Agrobacterium Tumefaciens* carrying mutated octopine Ti plasmids . . . ", *Gene*, vol. 14, pp. 33-50.

Wullems et al, 1981, "Retention of Tumor Markers in F1 Progeny Plants from in Vitro Induced Octopine and Nopaline Tumor Tissues", Cel, vol. 24, pp. 719-727.

Hoekema et al, 1984a, "Transfer of the Octopine T-DNA Segment to Plant Cells Mediated by Different Types of *Agrobacterium* . . . ", *J. Bact.*, vol. 158, pp. 383-385.

Leemans et al, 1981, "Site-Specific Mutagenesis of *Agrobacterium* Ti Plasmids and Transfer of Genes to Plant Cells", *J. Mol. App. Gen.*, vol. 1, pp. 149-164.

Garfinkel et al, 1981, "Genetic Analylsis of Crown Gall: Fine Structure Map of the T-DNA by Site-Directed Mutagenesis", *Cell*, vol. 27, pp. 143-153.

Joos et al, 1983, "Genetic Analysis of T-DNA Transcripts in Nopaline Crown Galls", Cell, vol. 32, pp. 1057-1067.

Yang et al, 1981, "Revertant Seedlings from Crown gall Tumors Retain a Portion of the Baterial Ti Plasmid DNA Sequences", Proc. Natl. Acad. Sci., vol. 78, pp. 4151-4155.

Hoekema et al, 1984b, "Delivery of T-DNA from the *Agrobacterium Tumefacens* Chromosome into Plant Cells", *EMBO J.*, vol. 3, 2485-90.

Otten et al, 1981, "Mendelian Transmission of Genes Introduced into Plants by the Ti Plasmids of *A. tumefaciens*",*Mol. Gen. Genet.*, vol. 183, 209-13.

Lippincott et al, 1969, "Bacterial Attachment to a Specific Wound Site as an Essential Stage in Tumor Initiation . . . ", *J. Bact.*, vol. 97, pp. 620-628.

(List continued on next page.)

*Primary Examiner*—Thomas G. Wiseman
*Assistant Examiner*—Karen Maurey
*Attorney, Agent, or Firm*—Fitch, Even, Tabin & Flannery

[57] ABSTRACT

The invention discloses an in vivo method for transforming and regenerating intact plants. According to the method, a plant (P) is infected with an infectious microbial agency comprised of: (1) virulence functions, (2) oncogenic factors capable of inducing a shoot-bearing shooty tumor on plant (P), and (3) a carrier vector containing engineered heterologous transfer DNA capable of being integrated into the nuclear DNA of plant (P) cells. Infected plant (P) is maintained until a shoot-bearing shooty tumor develops at or near the infection site. Those shoots, or progeny thereof, that contain transformed cells having heterologous transfer DNA integrated into their genomes are the selected and utilized to produce whole plants that contain cells having heterologous transfer DNA integrated into their genomes.

27 Claims, 2 Drawing Figures

OTHER PUBLICATIONS

Barton, K. A., et al., "Regeneration of Intact Tobacco Plants Containing Full Length Copies of Genetically Engineered T-DNA, and Transmission of T-DNA to R1 Progeny", *Cell,* vol. 32, 1033–1043, Apr. 1983.

Marcel DeCleene and Jozef DeLey, *The Botanical Review,* vol. 42, pp. 389–466, (1976).

deFramond, Annick J., Barton, Kenneth A., and Chilton, Mary-Dell, "Mini-Ti: A New Vector Strategy for Plant Genetic Engineering", *Biotechnology,* Apr. 1983, pp. 262–269.

Henri DeGreve, et al., "Regeneration of Normal and Fertile Plants that Express Octopine Synthase, from Tobacco Crown Galls after Deletion of Tumor Controlling Functions", *Nature,* vol. 300, pp. 752–755 (1982).

Hoekema, A., et al., "A Binary Plant Vector Strategy Based on Separation of vir- and T-region of the Agrobacterium tumefaciens Ti-plasmid", *Nature,* (Lond.) vol. 303, pp. 179–180 (1983).

Koekema, A., et al., "Agrobacterium tumefaciens and its Ti-Plasmid as Tools in Transformation of Plant Cells", *Plant Molecular Biology,* A. R. Liss, Inc., New York (1983), at pp. 2–22.

Leon A. B. M. Otten and Robert A. Schilperoort, "A Rapid Micro Scale Method for the Detection of Lysopine and Nopaline Dehydrogenase Activites", *Biochim. Biophys. Acta.,* vol. 527, pp. 497–500 (1978).

Schell, Josef and Van Montagu, Marc, "The Ti Plasmids as Natural and as Practial Gene Vectors for Plants", *Biotechnology,* Apr. 1983, pp. 175–180.

Simpson, Robert B., et al., "DNA Transfer to Plant Cells Using the Ti Plasmid Vector", *Plant Molecular Biology,* R. Liss, Inc. New York, (1983) pp. 23–24.

METHOD FOR PRODUCING INTACT PLANTS CONTAINING FOREIGN DNA

FIELD OF THE INVENTION

The present invention relates generally to a method for producing genetically engineered plants. More specifically the present invention relates to a method for producing whole plants that have been genetically engineered in vivo to contain foreign or heterologous DNA.

BACKGROUND OF THE INVENTION

Crown gall is a widespread neoplastic disease caused by the bacterial pathogen *Agrobacterium tumefaciens*. Most dicotyledons, some gymnosperms, and a few monocotyledons are susceptible to the disease. (DeCleene and DeLey, 1976). It is known that large plasmids in virulent Agrobacterium strains are essential for tumor formation in infected plants. Such plasmids are referred to as Ti or tumor-inducing plasmids. (Simpson, et al , 1983.)

It is not yet known exactly how the bacterial pathogen transforms wounded host plants so they produce crown gall tumors. However, it is known the Ti (and the Ri or root-inducing plasmids from *Agrobacterium rhizogenes*) contain a region of DNA called the vir or virulence region that must be functional if wild-type cells are to be transformed into tumor cells. It is also known the end result of such transformation is the integration of another plasmid portion, called the T-DNA or transfer-DNA, into the nuclear genome of the transformed cells. The vir gene region is not integrated into the plant genome. It is however presumed to code for substances necessary for T-DNA transfer or integration, or both. (Schell and Van Montagu, 1983.)

Although functional vir genes are essential for T-DNA transfer, the vir genes and the T-DNA do not have to be carried on the same Ti plasmid for transfer and integration of the T-DNA to occur. The vir genes and the T-DNA can be carried on separate plasmids contained within the same Agrobacterium (Schell and Van Montagu, 1983). In fact, the octopine T-DNA segment can be transferred to plant cells if it is carried by an Agrobacterium containing the vir genes from a nopaline Ti plasmid, a limited host range Ti plasmid or an Ri plasmid (Hoekema, et al., 1984).

Native T-DNA, as opposed to T-DNA that has been "engineered" by man or mutated by nature, usually contains specific DNA border sequence(s) that flank: (1) oncogenic or "onco" genes (necessary for tumor formation) and, (2) genes that code for specific metabolites known as opines. There are several types of opines, none of which is produced by normal, i.e. non-transformed, plant cells. The type of opine produced by the tumor tissue, as well as the pattern of its production, is determined by the type of Ti plasmid carried in the infecting Agrobacterium. (Bomhoff, et al., 1976.) Thus, on the basis of the opine made in the plant tumor cell, the Ti plasmids have been grouped into octopine, nopaline and agropine classes. (Ooms, et al., 1982). The opines, although synthesized by the tumor tissue, are catabolized by the infecting bacteria. (Bomhoff, et al., 1976.)

Crown gall tumor, whether grown in vivo or maintained in vitro on simple medium, does not differentiate into sexually mature plants. Instead the tumor grows in an undifferentiated form referred to as a callus. Unlike wild-type plant cells, transformed cells from callus do not require the addition of plant hormones (auxins and cytokinins) to the growth medium in order to grow in culture. Rather calli can be maintained in culture on a simple medium that is devoid of exogenous growth substances. Since the plant hormones are known to play key roles in plant cell proliferation and differentiation, this lack of differentiation in the crown gall tumors is believed due to a growth hormone imbalance caused by the transforming Ti plasmids. (Simpson, et al., 1983.)

The Ti plasmids are natural plant vectors because they can transfer prokaryotic T-DNA into the eukaryotic plant cell. In addition, foreign heterologous genes can be inserted into the T-DNA of a Ti plasmid and thus genetically engineered into the genome of a plant cell. As a result, current efforts to transfer foreign genes into plant cells are centered on the Ti plasmids. (deFramond, et al., 1983.)

Unfortunately the Ti plasmids are too large to allow foreign DNA to be inserted directly into the T-DNA region. (Since restriction sites unique to the T-DNA region do not exist on these large plasmids it is extraordinarily difficult to utilize a specific site for the insertion of the heterologous DNA.) As a result, smaller "engineered" Ti-type vectors having fewer restriction sites must be utilized.

Once the foreign DNA has been inserted into the T-DNA on these smaller vectors, the vectors can be used to transfer the engineered T-DNA into the plant cell genome. Alternatively, a binary plant vector system, based on the separation of the vir and T-DNA regions, can be used. The binary system utilizes the interaction of two plasmids, one containing the vir region and the other containing the T-DNA region on a wide-host-range replicon. (An *Agrobacterium tumefaciens* strain harboring both plasmids has a normal tumor-inducing capacity although neither plasmid is functional alone.) With this approach, the T-DNA on one plasmid can, because of its smaller size, be easily manipulated to contain heterologous DNA when a bacterium such as *Escherichia coli* is used as a host. Subsequent transfer of the engineered plasmid into an *Agrobacterium tumefaciens* strain harboring the plasmid with the vir region makes it possible to introduce the manipulated or engineered T-DNA into the plant cell genome. (Hoekema, et al., 1983a.)

Although the Ti plasmids offer great promise as plant gene vectors, a major obstacle to their generalized use has been the difficulty in regenerating whole plants from the transformed tumor cells. Most disclosed regeneration methods involve in vitro tissue culture techniques. See generally Hoekama, et al. (1983b.) Some of these methods utilize an initial in vivo infection step that is followed by in vitro regeneration of transformed cells obtained from the crown gall callus. Other methods utilize two in vitro techniques, one to infect plant cell protoplasts and the other to regenerate whole plants from the transformed protoplasts. However, since these methods rely on in vitro plant tissue culture techniques, they are time consuming and burdensome to carry out. In addition, regeneration from protoplasts or calli has only been shown to be possible for a small number of plants. (Simpson, et al., 1983.)

More useful methods for transformation and regeneration of plant cells are ones that utilize in vivo infection methods for transformation but eliminate the need for in vitro regeneration. Instead these methods rely on in vivo regeneration of whole plants from tumors. Unfortunately, attempts to develop such methods have not been very successful. As a result, the art to date contains only a few reported cases of successful regeneration of transformed plants from tumors.

At least one of the reported cases (DeGreve, et al., 1982) apparently involved a fortuitous deletion of the oncogenes carried on the Ti plasmids. (Absence of the oncogenes allowed the transformed plant cells to differentiate into whole phenotypically normal plants.) In another, prior inactivation of one of the oncogenes allowed the infected plants to regenerate. See Barton, et al. (1983). Unfortunately this and other methods that involve crippled or disabled oncogenes are especially unsatisfactory for generalized use for plant transformation and regeneration because oncogenes, though disarmed, remain in the plant. It is possible these genes could be activated at some future point in the lifetime of the transformed plant or of its progeny. Since activation of the "disarmed" oncogenes could cause undesirable phenotypic changes in the plant, their presence presents an undesirable risk to the plant breeder seeking improved varieties of crop plants. In addition, the low frequency and unpredictable nature of the deletion process makes it unsatisfactory as a general method for regenerating whole plants from tumors.

Thus there has been a failure of past efforts to provide an in vivo method for transforming and regenerating whole plants from tumors wherein the plants are transformed to contain foreign DNA but not disabled oncogenes.

OBJECTS OF THE INVENTION

It is an object of the present invention to provide an in vivo method for transforming and regenerating whole plants that contain cells having heterologous DNA integrated into their nuclear genomes.

It is a further object of the present invention to provide an in vivo method for transforming and regenerating whole plants from tumors wherein the whole plants do not contain oncogenes, even disarmed oncogenes, but do contain cells having heterologous DNA integrated into their nuclear genomes.

It is a further object of the present invention to provide an in vivo method for transforming plant cells wherein the method utilizes engineered Agrobacterium tumefaciens Ti-type plasmids as carrier vectors for the transforming heterologous DNA that is to be integrated into the plant cells' nuclear genomes.

It is a further object of the present invention to provide an in vivo method for transforming plant cells wherein the method further utilizes *Agrobacterium* vir functions in conjunction with the engineered Ti-type carrier vectors.

It is a further object of the present invention to provide an in vivo method for transforming and regenerating whole plants wherein the method utilizes crown gall shooty tumors as a means of regenerating whole plants from tumors.

It is a further object of the present invention to provide an in vivo method for transforming and regenerating whole plants wherein the method further utilizes the *Agrobacterium tumefaciens* shooty mutants in conjunction with Agrobacterium vir functions and Ti-type carrier vectors.

Other objects of the present invention will become apparent to those skilled in the art from the following description and figures, wherein:

FIG. 1 is a schematic diagram illustrating construction of Ti-type carrier vector pARC2; and FIG. 2 is a schematic diagram illustrating construction of Ti-type carrier vector pARC4.

SUMMARY OF THE INVENTION

Very generally the invention discloses an in vivo method for transforming and regenerating intact plants. According to the method, a plant (P) is infected with an infectious microbial agency comprised of: (1) virulence functions, (2) oncogenic factors capable of inducing a shoot-bearing shooty tumor on plant (P), and (3) a carrier vector containing engineered heterologous transfer DNA capable of being integrated into the nuclear DNA of plant (P) cells. Infected plant (P) is maintained until a shoot-bearing shooty tumor develops at or near the infection site. Those shoots, or progeny thereof, that contain transformed cells having heterologous transfer DNA integrated into their genomes are then selected and utilized to produce whole plants that contain cells having heterologous transfer DNA integrated into their genomes.

According to the invention the shoots can be allowed to develop into sexually mature plants without being removed from the tumor. Alternatively the shoots can be excised and allowed to grow and mature "in pots". Also according to the invention, either the shoots, or the progeny thereof, can be identified as having been transformed. More specifically, according to one aspect of the invention, fertile shoots containing cells having heterologous transfer DNA integrated into their genomes are identified and then propagated by means of sexual reproduction to produce transformed whole plants. According to another aspect of the invention, $F_1$ progeny are obtained from self-fertilized shoots on the plant (P) shooty tumor. The $F_1$ progeny that contain transformed cells having engineered heterologous transfer DNA integrated into their genomes are identified and then propagated by sexual reproduction.

The invention discloses novel carrier vectors used to transform plant cells. The invention also encompasses plants, including the individual plant cells and seeds thereof, transformed and regenerated by means of the novel method disclosed herein.

DETAILED DESCRIPTION OF THE INVENTION

Figure 1:
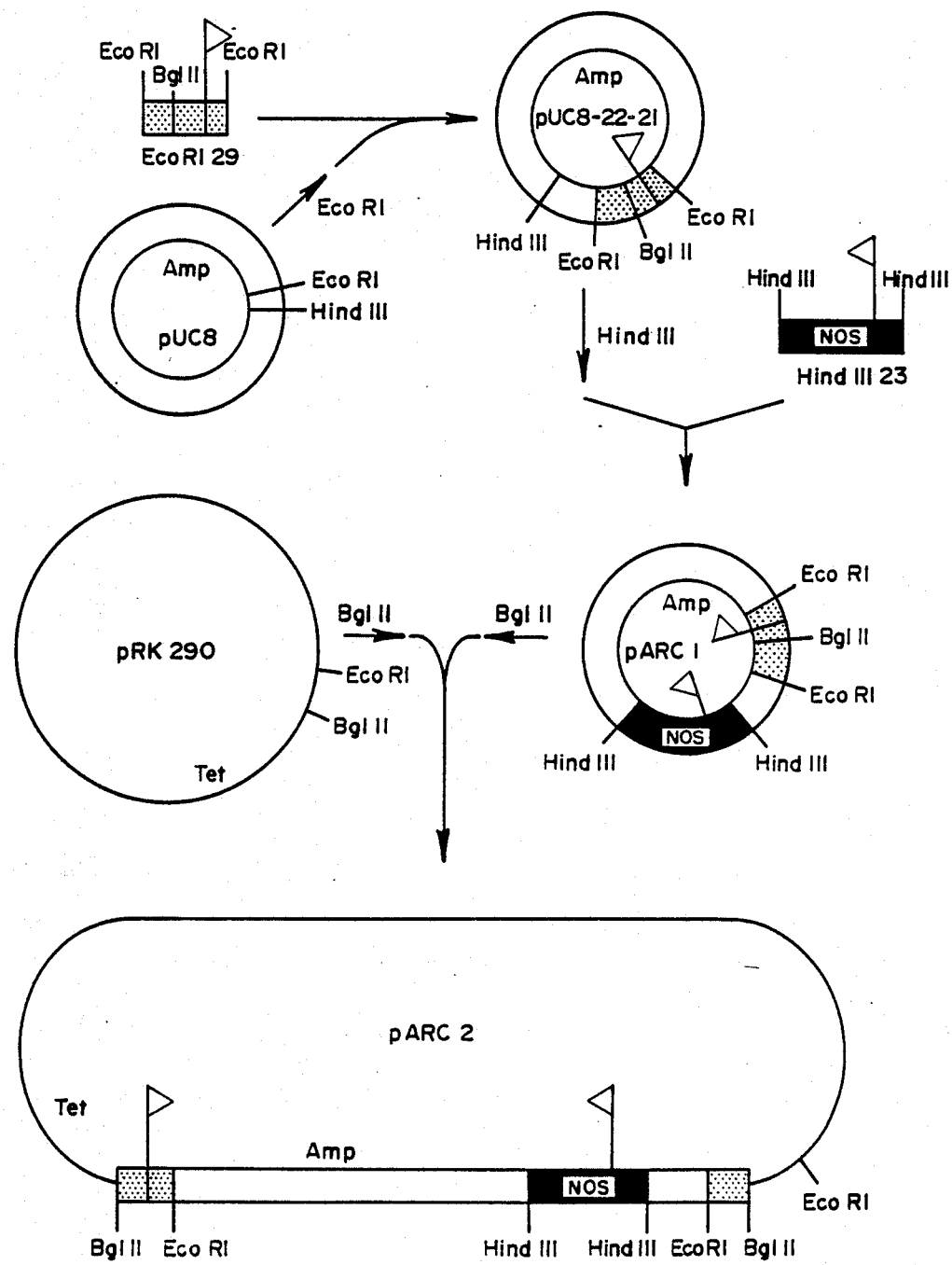

The present invention discloses an in vivo method for transforming and regenerating whole plants from tumors. The method of the invention utilizes an "engineered" Agrobacterium Ti-type carrier vector as the in vivo means of transferring "engineered heterologous DNA-bearing T-DNA" into the plant cell genome. The invention further utilizes a "shooty mutant mechanism" as the in vivo means of regenerating whole plants from tumors.

The in vivo method of the invention can be used for the transformation of any plant (P) as long as the plant forms a shooty tumor following infection with an *Agrobacterium tumefaciens* shooty mutant strain. (See De-Greve, et al., (1982) for a report on shooty tumors in tobacco, Ooms, et al. (1983) for a report of shooty tumors on potatoes and Leemans, et al. (1982) for a report of shooty tumors on petunias.) It is known that most dicotyledons, some gymnosperms and a few monocotyledons (Liliales and Arales) are susceptible to crown gall disease. (DeCleene and DeLey, 1976.) It is also known that *Agrobacterium tumefaciens* strains bearing nopaline or octopine Ti plasmids with mutations in one T-DNA oncogene locus, referred to as the tms locus, are "oncogenic" but cause "shooty" rather than "normal" crown gall tumors (Ooms, et al., 1981 and Joos, et al., 1983). The Agrobacterium strains that cause shoot-bearing tumors are called "shooty" mutant strains. Any shooty mutant strain can be used in the method of the present invention as long as it produces shooty tumors on the plants to be transformed.

The invention does not require that the shooty mutant strains be identified or understood at the "genetic level" before they can be used in the disclosed method. Instead useful mutant strains can be identified at a "gross level" simply by their ability to cause shooty tumors. More specifically, a strain whose genetic make-up is unknown can be used to infect the plant to be transformed. If the unknown strain causes a shooty tumor on the infected plant, the strain can be presumed to be a mutant suitable as a source of "oncogenic factors" responsible for inducing a shoot-bearing shooty tumor on the infected plant. For purposes of the present invention the term "oncogenic factors" is defined functionally, i.e., it means factor(s) contributed by the Agrobacterium shooty mutant strains that are responsible for inducing a shoot-bearing shooty tumor on the infected plant.

The present invention builds on the fact that some as yet unknown mechanism (referred to herein as the "shooty mutant mechanism") in the shooty tumor leads to the formation of shoots. The shooty mutant mechanism may be a hormone imbalance caused by a mutation at the tms locus. (Ooms, et al., 1981). However, for purposes of this invention, the "shooty mutant mechanism" need not be understood. All that matters is that a given shooty mutant strain be able to cause a shoot-bearing shooty tumor on the plant (P) to be transformed.

The present invention also builds on the finding that fortuitous deletions in the T-DNA of some shooty mutants result in transformed shoots that root and develop into normal and fertile plants. See Otten, et al. (1981). However, to avoid the unpredictability of the fortuitous deletion process, and the undesirability of having oncogenes, even disarmed ones in the transformed plants, the present invention, for the first time, teaches infecting a plant with an infectious agency that separates the shooty mutant oncogenic factors from the engineered T-DNA. More specifically, as the means of predictably transforming shoots on the shooty tumor so they contain cells having heterologous DNA integrated into their genomes, the method of the invention utilizes an infectious microbial agency comprised of "oncogenic factors" capable of inducing a shoot-bearing shooty tumor on the plant (P) being transformed, "virulence factors" necessary for transfer and/or integration of heterologous "engineered" T-DNA into the plant cell genome, and an "engineered" Ti-type carrier vector bearing the heterologous T-DNA that is to be transferred to the plant cell genome. As a result of the combination of elements that comprise the unique infectious microbial agency disclosed herein, the oncogenic factors can still be used to cause the shooty tumor, and the "shooty tumor mechanism" can still be used for the formation of shoots. Although most of the shoots that grow from the shooty tumor will not be transformed (DeGreve, et al., 1982), again because of the unique combination of elements in the disclosed infectious microbial agency, some of the shoots will be transformed and will contain cells having engineered heterologous T-DNA integrated into their genomes. Such cells will not contain any oncogenes, even disabled ones, since the heterologous T-DNA was not engineered to include them.

For purposes of this invention "virulence factors" are defined as functional portions on Agrobacterium Ti or Ri plasmids which, when inactivated, prevent transfer and/or integration of T-DNA into the plant cell genome. Thus, for purposes of the invention, any mutant strain capable of inducing a shoot-bearing shooty tumor will necessarily carry "virulence functions" since by definition virulent means highly infectious or capable of forming a tumor. In other words, if a mutant strain induces a shoot-bearing shooty tumor, the strain will by definition be virulent since it caused formation of the tumor. As a result, the virulence functions needed for transfer and integration of the "engineered" T-DNA will be inherently supplied by the shooty mutant strain used to induce the shooty tumors. Alternatively, carrier vectors with their own vir portions could be utilized as a supplemental source of the necessary virulence functions.

In addition to the vir functions and the oncogenic factors, the disclosed infectious microbial agency includes an engineered carrier vector that contains heterologous transfer DNA (h/T-DNA). More specifically, the carrier vector contains "engineered" transfer DNA comprised of T-DNA border sequence(s) and heterologous DNA fragments to be integrated into the plant cells' nuclear genomes. The carrier vector will also preferably include a broad-host-range replicon to facilitate insertion of the heterologous DNA into the vector. The host range will preferably include *Escherichia coli* and *Agrobacterium tumefaciens* strains. In preferred forms, the carrier vector will not include any oncogenes, even disabled or disarmed ones. Any carrier vector capable of transferring T-DNA to the plant cell genome can be utilized in the method of the invention. Disclosed carrier vectors pARC2 and pARC4, which do not contain oncogenes, even disabled ones, are preferred.

The heterologous DNA to be transferred into the plant cell genome will be flanked by T-DNA border sequence(s). For purposes of the invention, any Ti border sequence(s), native or synthesized, can be used to flank the heterologous DNA as long as the border sequence(s) function to integrate the T-DNA into the plant cell genome. The Ti border sequences from Ti plasmid pTiT37 (Yang and Simpson, 1981) are preferred.

The heterologous DNA within the T-DNA border sequences can be comprised of any DNA capable of being inserted into the carrier vector. Such DNA will preferably be from 1 to 50,000 base pairs in length and will preferably comprise two or more genes. One of the two or more genes will preferably code for a substance that provides the basis for transformation selection (e.g., a marker gene). The other gene or genes will preferably code for function(s) or trait(s) unrelated to the selection process. Such functions can include improved resistance to pests and pathogens, improved tolerance to weather and poor soil, increased seed protein production, etc.

According to the method of the invention, a plant (P) is infected with the infectious microbial agency and then maintained until a shoot-bearing shooty tumor develops at or near the infection site. Any plant capable of forming a shooty tumor can be used. In a preferred form, the plant is infected by wounding and then the wound site is used to introduce the infectious microbial agency into the plant. Alternatively the infectious microbial agency could be introduced by such techniques as microinjection.

Plant (P) can be wounded by any method known to the art. Such methods include cutting, scraping, abrading, and decapitating. Any part of the plant can be wounded, including leaves, stems and roots. In a preferred form, plant (P) stems are cut or decapitated and then infected with the infectious microbial agency. Preferred methods for wounding and infecting plants are described in the Preparative Methods section, infra.

The infected plants are preferably maintained in a greenhouse under controlled environmental conditions until the shoot-bearing shooty tumors develop. Preferred maintenance methods are also described in the Preparative Methods section, infra.

Both transformed and untransformed shoots grow on the shooty tumors. For purposes of this invention it is possible that some shoots will contain T-DNA derived from the "shooty mutants" while others will contain T-DNA derived from the engineered transfer vectors. The T-DNA derived from the engineered transfer vectors is referred to herein as "h/T-DNA". h/T-DNA transformed shoots will contain cells having engineered heterologous T-DNA integrated into their genomes. h/T-DNA transformed shoots can be identified directly by analyzing for the presence of the engineered heterologous T-DNA. Alternatively the h/T-DNA transformed shoots can be identified by indirect methods that test for the presence of a marker gene product, e.g., antibiotic resistance, if the engineered T-DNA carries an antibiotic resistance gene, or by enzyme analysis, if the engineered T-DNA codes for an enzyme unique to the transformed shoots. Novel carrier vectors pARC2 and pARC4 disclosed herein contain engineered h/T-DNA that codes for nopaline synthase. These carrier vectors are preferably utilized with an octopine producing shooty mutant strain so the engineered h/T-DNA transformed shoots can be identified by the presence of nopaline. Methods for detecting nopaline are described in the Preparative Methods section, infra.

According to one aspect of the invention, fertile shoots containing cells having engineered heterologous transfer DNA (h/T-DNA) integrated into their genomes are identified and then propagated by sexual reproduction. In this aspect of the invention the transformed shoots are not removed from the tumor prior to propagation. Instead the shoots containing engineered h/T-DNA are allowed to flower while still on the tumor. The flowers are self-pollinated and the resulting seeds are germinated on filter paper or in a standard soil mixture. The seedlings are then transplanted to pots for further growth and propagation.

In another aspect of the invention shoots from the shooty tumor are excised, rooted in sterile sand and then transplanted to pots containing a standard soil mixture. These potted shoots are allowed to mature and flower; then they too are self-pollinated. Seeds from the self-pollinated plants are set and allowed to germinate to produce $F_1$ progeny or seedlings, some of which will contain h/T-DNA.

The $F_1$ plants containing h/T-DNA are then self-pollinated to produce $F_2$ plants. Based on the finding of Otten, et al. (1981) that inserted T-DNA can be stably maintained, expressed and sexually transmitted by transformed plants, it is expected that some of the $F_2$ seedlings will also contain cells having h/T-DNA integrated into their genomes.

The efficacy of the method of the invention is illustrated in an example that utilizes tobacco plants and a "mixed" infectious microbial agency comprised of a pARC2 carrier vector and an *Agrobacterium tumefaciens* octopine-type shooty mutant strain. Tobacco was utilized to demonstrate the usefulness of the disclosed method because tobacco is relatively easy to infect. In addition, large shooty tumors grow on wounded tobacco stems following infection by "shooty mutants". It should be understood that the method of the invention is applicable to any plant capable of forming shoot-bearing "shooty tumors". The tobacco example is presented for illustrative purposes only; it is not intended to limit the scope of the invention in any way.

The preparative methods utilized herein are listed below.

PREPARATIVE METHODS

Bacterial Strains and Plasmids

The bacterial strains and plasmids utilized herein are listed in Tables I and II, infra.

Plasmid pBstEII 9,14 carries EcoRI fragment 29 derived from Ti plasmid pTiT37. EcoRI fragment 29 contains the left terminus or border sequence of the T-DNA region which, on this fragment, is located approximately 100 base pairs (bp) from the right end of the fragment. (Yadav, et al., 1982, Zambryski, et al., 1980, 1982). Plasmid pBstEII 9,14 resulted from the partial digestion of pTiT37 DNA with BstEII and ligation of the resulting fragments to the vector pMB9 (Yang and Simpson, 1981); the insert consists of the adjacent BstEII fragments 9 and 14.

Plasmid pUC8 (Vieira and Messing, 1982) was obtained from Bethesda Research Laboratories, Gaithersburg, MD 20877.

Plasmid pT37H23 carries HindIII fragment 23 derived from Ti plasmid pTiT37. From left to right HindIII fragment 23 contains the 5' portion of the DNA encoding transcript 6b (Willmitzer, et al. 1983), the entire nopaline synthase or NOS gene (Bevan, et al., 1983, Depicker, et al., 1982), the right terminus T-DNA sequence (Yadev, et al., 1982; Zambryski, et al., 1980, 1982), and a portion of the Ti plasmid which is not transferred to plant cells. Plasmid pT37H23 (Depicker, et al., 1982) was a generous gift from Scott Stachel.

Vector Construction

The restriction enzymes utilized herein were also from Bethesda Research Laboratories. They were used according to the manufacturer's instructions. The procedure for transformation of *Escherichia coli* with plasmid DNAs is described in Alexander, et al. (1984). Other manipulations of nucleic acids are essentially those described by Maniatis, et al. (1982) unless otherwise indicated.

Figure 2:
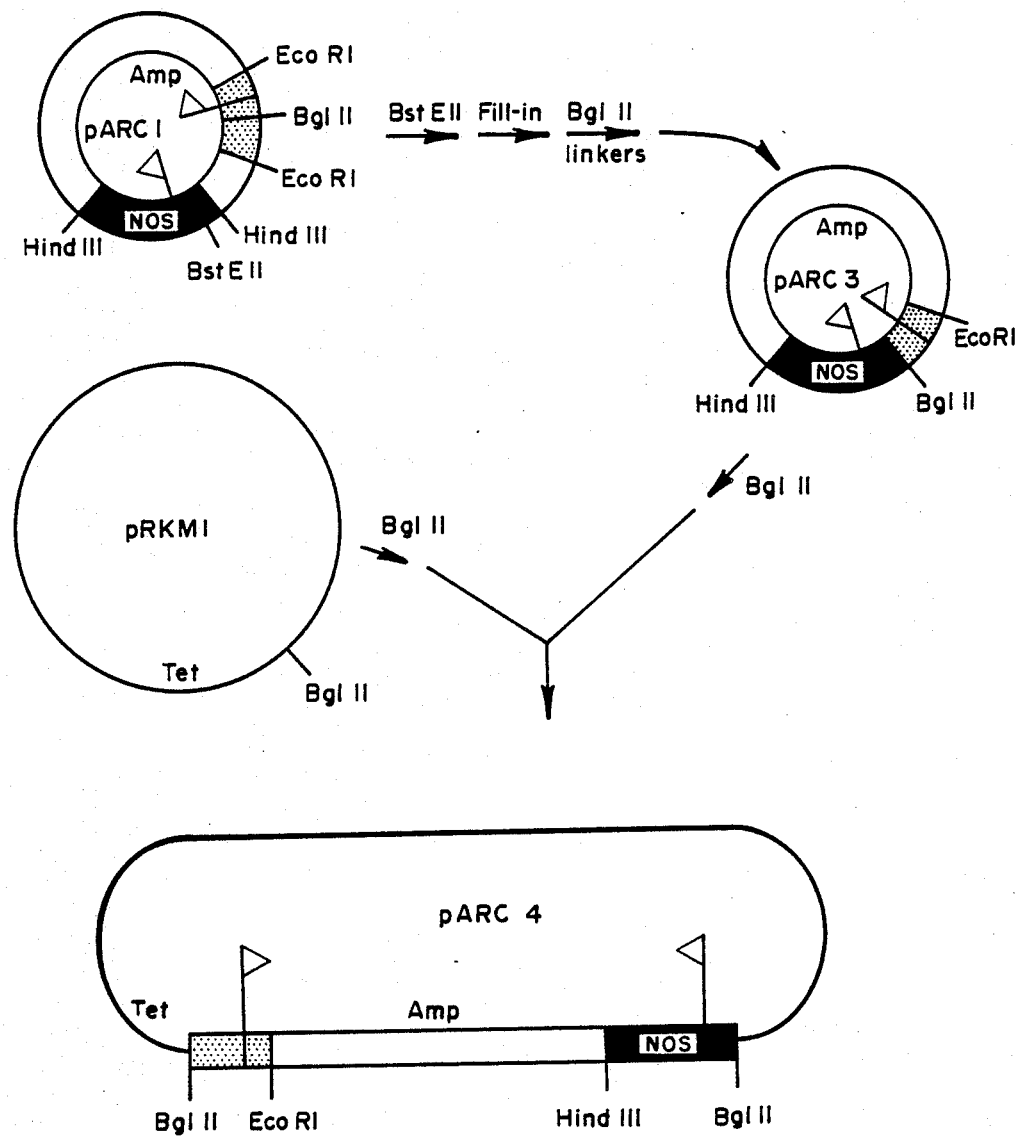

Engineered wide-host-range plasmids pARC2 and pARC4 were constructed in steps that required the sequential construction of intermediate plasmids pUC8-22-21, pARCand pARC3. These steps are illustrated schematically in FIGS. 1 and 2. In the figures, the right and left T-DNA terminus sequences are indicated with flags.

Intermediate plasmid pUC8-22-21 is comprised of the 1.5 Kb EcoRI fragment from pTiT37 inserted into pUC8. In creating pUC8-22-21, EcoRI fragment 29 was cloned into the EcoRI site of pUC8 in the following manner. DNA fragments from an EcoRI digest of pBstEII 9,14 (Yang and Simpson, 1981) were mixed with an EcoRI digest of pUC8. After ligase treatment, the mixture was transformed into *Escherichia coli* strain JM83. Colorless colonies (See Vieira and Messing, 1982) were selected on plates containing Luria agar (Maniatis, et al., 1982), supplemented with 40 micrograms/ml ampicillin and 35 micrograms/ml X-gal. One of the colonies contained cells carrying the plasmid designated pUC8-22-21.

EcoRI fragment 29 in pUC8-22-21 is oriented with the left terminus sequence distal to the HindIII site of pUC8. Fragment identification and orientation was based on the HincII site mapped by Zambryski, et al. (1980) approximately 480 base pairs from the right end of EcoRI fragment 29. Fragment identification was verified by DNA sequence analysis.

Intermediate plasmid pARC1 is comprised of HindIII fragment 23 from pTiT37 inserted into the HindIII site of pUC8-22-21. pARC1 was constructed in the following manner. HindIII fragment 23, which contains the T-DNA right terminus sequence, was isolated by digesting plasmid pT37H23 with HindIII. The restriction fragments were then subjected to electrophoresis through an agarose gel and electro-elution onto nitrocellulose as described in Maniatis, et al. (1982). (Plasmid pT37H23 contains HindIII fragment 23 from pTiT37 inserted into the HindIII site of pBR322. See Depicker, et al. (1982)). Purified HindIII fragment 23 was then ligated to HindIII-digested pUC8-22-21. The mixture was transformed into *Escherichia coli* strain HB101, and ampicillin-resistant colonies were selected. Cells from one of these colonies contained the plasmid designated pARC1. Plasmid pARC1 has HindIII fragment 23 inserted into the HindIII site of pUC8-22-21; the fragment is oriented with the right terminus sequence near the EcoRI insert site. See FIG. 1.

Plasmid pARC2 is a derivative of pARC1. It was produced by linearizing pARC1 with BglII and then inserting the linearized fragment into the BglII site of the broad-host-range vector pRK290. The structure of pARC2 is such that the right and left T-DNA terminus sequences have the same direction and orientation with respect to each other as they did in Ti plasmid pTiT37; however, in pARC2 the major portion of the T-region, including all of the oncogenes, has been replaced by pUC8. The broad-host-range replicon from pRK290 permits pARC2 to replicate in Agrobacterium as well as *Escherichia coli.* Like pRK290 (Ditta, et al., 1980), pARC2 can be mobilized by the helper plasmid pRK2013. (This ability was used in some cases to transfer the vector to Agrobacterium strains; alternatively, Agrobacterium strains were transformed (Holsters, et al., (1978) with pARC2 DNA.)

To construct plasmid pARC2, products from a BglII digestion of pARC1 and from a BglII digestion of the broad-host-range vector pRK290 were mixed, ligated and then transformed into *Escherichia coli* strain HB101. Following its isolation from this *Escherichia coli* strain, pARC2 plasmid DNA was purified and then transformed, as described by Holsters, et al. (1978), into Agrobacterium strains A136 and A328 to produce strains A136 (pARC2) and A328 (pARC2) respectively. Strain LBA4404 (pARC2) was isolated from a mating mixture containing LBA4404, HB101 (pRK2013) and HB101 (pARC2) using a procedure described by Garfinkel, et al. (1981).

Plasmid pARC4 is similar to pARC2 except that pARC4 contains unique EcoRI and HindIII sites within the engineered T-DNA region to facilitate in vitro insertion of foreign DNA fragments. The first step in constructing pARC4 was to digest pARC1 with BstEII. The digestion products were then "filled in" with DNA polymerase I Klenow fragment and all four deoxynucleoside triphosphates. BglII linkers (New England Biolabs, Beverly, Mass. 01915) were added using T4 DNA ligase and then the products were digested with BglII. After a ligation step and transformation of *Escherichia coli* strain HB101, plasmid pARC3 was isolated. See FIG. 2.

Plasmid pARC4 is a derivative of plasmid pARC3 and a plasmid designated pRKM1. It was constructed in the following manner. The plasmids pRKM1 and pARC3 were separately digested with BglII. (Plasmid pRKM1 was constructed by T. D. McKnight (personal communication) by digesting the broad-host-range vector pRK290 with EcoRI, "filling-in" with DNA polymerase I Klenow fragment and deoxynucleoside triphosphates and reclosing with T4 DNA ligase. This eliminated the EcoRI site.) The pRKM1 and pARC3 digestion products were then ligated to produce pARC4. See FIG. 2. Agrobacterium strains LBA4404 (pARC4) and A328 (pARC4) were constructed using the mating procedure described above.

Virulence Tests

Procedures described by Garfinkel and Nester (1980) were used for virulence tests on carrot/*Daucus carota* disks, tobacco/*Nicotiana tabacum* and Kalanchoe diagramontania.

Inoculation of Plants

A single colony of an Agrobacterium strain was inoculated into LB broth (Maniatis, et al., 1982) and grown at 28° C. with shaking until late stationary phase (measured with a Klett-Summerson photoelectric colorimeter equipped with a green filter, #54). When two different strains were to be mixed, the more concentrated suspension was diluted so it equalled the concentration of the more dilute suspension (5–20 x 10E8 bacteria per ml). Following such dilutions the mixtures were made at the indicated ratios. The bacterial mixtures, as well as individual cultures, were then pelleted.

Stems from plants (tobacco) 18 to 24 inches high were wounded by making a slit in the stem with either a sterile wooden stick or a razor blade. A razor blade was used when a stem was to be decapitated. Bacterial pellets were applied to the wounds using either a broken stick or a toothpick as a spatula. The wounds were then wrapped with PARAFILM (TM, American Can Co., Greenwich, Conn. 06833) to keep them moist.

Maintenance of Plants

Plants were grown in a greenhouse and fertilized with VERDISOL 20-20-20 (TM, Moyer Chemical Co., Fresno, Calif. 93710) at 150 ppm nitrogen. In some cases, shoots arising from a tumor were excised with a razor blade, dipped in ROOTONE (TM, Union Carbide Agricultural Products Co., Inc., Ambler, Pa. 19002), rooted in sterile sand, and transplanted to pots containing a standard soil mixture of 33% sphagnum peat, 33% vermiculite, 33% SUPERSOIL (TM, Rod McLellan Co., So. San Francisco, Calif.). Flowers from both excised and unexcised shoots were self-pollinated and seeds were germinated on filter paper or in a standard soil mixture. Seedlings were transplanted to pots containing a bedding mix of peat, sand and pumice rock (Shelton Transfer Co., San Jose, Calif.).

Nopaline Assay

Leaves Weighing 0.1 to 0.5 g were frozen in liquid nitrogen, ground using a mortar and pestle, transferred to a 1.5 ml Eppendorf tube and mixed with 50 microliters ethanol per 0.1 g tissue. After 15 min. at room temperature, the debris were pelleted for another 15 min. in an Eppendorf centrifuge. 50 microliters of the supernatant were pipetted onto filter paper discs prepared with a hole-punch and Whatman #3 paper. After the discs were dry, they were placed at the origin prior to high voltage paper electrophoresis and staining essentially as described by Otten and Schilperoort (1978).

DNA Assay

Small amounts of plant DNA were isolated as follows: About 1 g of washed leaves was frozen in liquid nitrogen, ground to a powder with a mortar and pestle, transferred to a tube and then thawed in the presence of 4 ml lysis buffer (7 M guanidine HCl, 2% SARKOSYL, 20 mM EDTA, 20 mM Tris HCl, pH 8.0) (SARKOSYL, TM for SIGMA Chemical Co., St. Louis, Mo. 63178). After 1 hour at 55° C., 0.8 ml of water was added and the tube was spun at 4° C. for 20 min. at 20,000 rpm in a Sorvall SS34 rotor. The supernatant was brought to 5 ml with lysis buffer (4 vol. diluted with 1 vol. water) and then layered on a CsCl two step gradient. The CsCl steps were 3 ml each. They contained 20 mM Tris-HCl, pH 8.0 and 0.5 mg/ml ethidium bromide; they had a density of either 1.35 or 1.6 g/cc. The gradients were spun at 20° C. for at least 16 hr. at 38,000 rpm in a Beckman SW41 rotor. The band of DNA, which was visible with ultraviolet light at the interface between the steps, was removed. The DNA was extracted several times with isoamyl alcohol to remove the ethidium bromide. It was precipitated with isopropanol and with ethanol, and then resuspended in 50 microliters 1 mM EDTA and 10 mM Tris-HCl, pH 8.0. Isolation of larger amount of DNA will be performed essentially as described by White, et al. (1982).

Slot blot analysis was performed on the "Minifold II" apparatus using manufacturer's instructions (MINIFOLD, TM, Schliecher and Schuell, Keene, N.H. 03431). Southern blot analysis (Southern, 1975) was performed essentially as described by Thomashow, et al. (1980). The 32p-labeled RNA probe was prepared using the RIBOPROBE SP6-derived transcription system according to the instructions of the manufacturer. (RIBOPROBE, TM, Promega-Biotec, Madison, Wis. 53711.)

EXAMPLE

This example illustrates in vivo transformation and regeneration of whole plants containing heterologous DNA.

Whole tobacco plants were transformed and regenerated in vivo according to the methods of the present invention. The transformed and regenerated tobacco plants contain cells having heterologous DNA, coding for nopaline synthetase, integrated into their nuclear genomes. The various procedures utilized in the tobacco transformation and regeneration processes are discussed below.

Infectious Microbial Agency Vir Functions

The vir functions were supplied by Agrobacterium strain LBA4404. (LBA4404 contains a severely deleted Ti plasmid that has no T-DNA region (Ooms, et al., 1980)). However, despite the deletion, LBA4404 can incite tumors when it carries "native" T-DNA on a separate plasmid (Hoekema, et al., 1983; deFramond, et al., 1983).

Oncogenic Factors

The oncogenic factors were supplied by Agrobacterium strain A328. (A328 produces the tms or "shooty" tumor phenotype on tobacco stems (Garfinkel, et al., (1981)).

Carrier Vector

In this study pARC2 was used as the carrier vector to transport engineered heterologous T-DNA (h/T-DNA) into the genome of the tobacco plant cells. The "engineered h/T-DNA" in pARC2 does not contain any oncogenes but does contain the entire nopaline synthase (or NOS) gene. See FIG. 1. Since nopaline synthase is the enzyme which catalyzes the synthesis of nopaline in "NOS" transformed cells, transformed plants containing h/T-DNA will produce nopaline.

Infection

For this study plasmid pARC2 was inserted into LBA4404 to produce strain LBA4404 (pARC2). In another set of experiments, strain LBA4404 (pARC2) was used to infect tobacco, carrot disks, and Kalanchoe. As expected, since no oncogenes were present, strain LBA4404 (pARC2) did not incite tumors on any of the plants tested. Instead, the strain produced a response similar to avirulent strains LBA4404 and A136.

In the present study Agrobacterium strain LBA4404 (pARC2) was mixed with "shooty" mutant strain A328 to create a "mixed infection" type of infectious agency. For the "mixed infection" type of agency, the ratio of avirulent LBA4404 (pARC2) bacteria to virulent A328 bacteria was varied from about >100:1 to 1:1. (It was speculated that an increase in the number of avirulent LBA4404 (pARC2) bacteria would result in an increase in the number of plant cells receiving the "engineered h/T-DNA". However, it was known that inoculation of too many avirulent LBA4404 (pARC2) in the presence of too few virulent A328 might not lead to tumor formation because too few plant cells would be transformed by A328. Such reduced virulence through competition by avirulent bacteria has been reported (Lippencott and Lippencott, 1969).

For the present study, tobacco plants (stems from plants 18 to 24 inches high) were wounded and infected with the "mixed infection" type of infectious agency using the procedures disclosed in the Preparative Methods section, supra. An analysis of the infected plants revealed that tobacco stems infected with 100 or more avirulent LBA4404 (pARC2) to each virulent A328 did not exhibit any tumors and therefore did not exhibit any shoots. However, infections with as many as ten LBA4404 (pARC2) to each A328 did produce "shooty" tumors on the tobacco stems. Therefore, for purposes of this invention, a "mixed infection" comprised of avirulent vector bearing bacteria and virulent bacteria at ratios of about 10:1 to about 1:1 are preferred.

In a separate "single infection" experiment, pARC2 was introduced into virulent Agrobacterium strain A328 to produce strain A328 (pARC2). Wounded tobacco stems infected with A328 (pACR2) produced "shooty" tumors thus illustrating the efficacy of the "single infection" method. In another set of "single infection" experiments, strain A328 (pARC2) was used to infect carrot disks and Kalanchoe. As expected, since oncogenes are present, strain A328 (pARC2) incited tumors on all plants tested. Nopaline was detected in some of the tumor tissue indicating at least a portion of pARC2 DNA is transferred to plant cells.

Maintenance

Infected plants were grown in the greenhouse under controlled environmental conditions. In most cases the shoots were not removed from the tumors prior to sexual propagation. In some cases, shoots growing from the tumors were excised and rooted in sand as described in the Procedural Methods section, supra, prior to sexual propagation. They are referred to herein as "potted shoots".

T-DNA Assays

The "engineered h/T-DNA" in pARC2 contains the complete nopaline synthase (or NOS) gene. Therefore, shoots transformed with pARC2 T-DNA will contain nopaline. (Virulent A328 bacteria, on the other hand, produce octopine-containing tumors).

To identify plants containing "engineered h/T-DNA" from pARC2, leaves from plants derived from shoots on the shooty tumors were analyzed for the presence of nopaline. Some of the leaves contained nopaline, indicating that some of the plants had been transformed to contain h/T-DNA. Plants bearing leaves that contain nopaline are referred to herein as "nopaline positive plants."

The nopaline assay is an indirect test for the presence of "engineered h/T-DNA" from pARC2. To directly test for its presence, DNA samples (isolated by the rapid isolation procedure disclosed in the Procedural Methods section, supra) from nopaline positive plants and from control shoots were screened using slot blots. (See Procedural Methods, supra.) For the slot blot analysis the DNA was denatured, then focused through a slot onto nitrocellulose where it was attached by baking.

Hybridization with a radioactive RNA probe homologous to pUC8 identified the DNA samples (i.e. the plants) that contained at least a portion of the "engineered h/T-DNA" from pARC2. The intensity of the hybridization relative to standards suggests that in the transformed cells the number of "engineered h/T-DNA" copies per haploid genome varies from less than one to about five.

The structure of the "engineered h/T-DNA" in nopaline positive plants (i.e. plants transformed and regenerated according to the methods of the invention) is being examined using Southern blot analysis. It is expected that all of the "engineered h/T-DNA" from pARC2, from the left terminus sequence to the right terminus sequence, will have been transferred intact in most instances.

Transfer of "Engineered T-DNA" Through Meiosis

Flowers which developed on transformed shoots were self-pollinated. The resulting $F_1$ seedlings have been germinated and will be tested for the presence of "engineered h/T-DNA".

TABLE I

| PLASMIDS | | |
|---|---|---|
| PLASMID | DESCRIPTION | REFERENCE |
| pBstEII 9,14 | pTiT37 BstEII fragments 9 & 14 cloned in pMB9 | Yang & Simpson (1981) |
| pUC8 | AmpR | Vieira & Messing (1982) |
| pT37H23 | AmpR; pTiT37 HindIII fragment 23 cloned into pBR322 | Depicker, et al. (1982) |
| pUC8-22-21 | AmpR; pTiT37 EcoRI fragment 29 cloned into pUC8 | Described herein |
| pRK290 | IncP; TetR | Ditta, et al. (1981) |
| pRK2013 | IncP; KanR; can mobilize pRK290 and its derivatives | Ditta, et al. (1981) |
| pARC1 | AmpR; pTiT37 HindIII fragment 23 cloned into pUC8-22-21 | Described herein |
| pARC2 | pARC1 cloned into BglII site of pRK290 | Described herein |
| pRKM1 | pRK290 with EcoRI site eliminated | T. D. McKnight (unpublished) |
| pARC3 | Deletion derivative of pARC1 | Described herein |
| pARC4 | pARC3 cloned into BglII site of pRKM1 | Described herein |

| BACTERIA | | |
|---|---|---|
| STRAIN | DESCRIPTION | REFERENCE |
| *ESCHERICHIA COLI* STRAINS | | |
| HB101 | F—, hsdS20(rB-mB-),recA13,ara-14,proA2 lacY1,galK2,rpsL20(SmR),xyl-5,mtl-1, | Boyer and Roulland-Dussoix (1969) |

TABLE I-continued

| | | |
|---|---|---|
| JM83 | supE44, lambda-ara,del lac-pro,strA,thi,Phi80dlacZ del M15 | Vieira & Messing (1982) |
| *AGROBACTERIUM TUMEFACIENS* STRAINS | | |
| A136 | NalR, RifR, Vir−; no pTi | Garfinkel, et al. (1981) |
| A348 | pTiA6NC;NalR,RifR, Vir+ | Garfinkel, et al. (1981) |
| A328 | pTiA6NC::Tn5 no.328;NalR,RifR, KanR, Vir+,tms | Garfinkel, et al. (1981) |
| LBA4404 | Occ-,Vir−,SmR | Ooms, et al. (1982) |

Reference List

The references referred to herein are listed below.

1. Alexander, D. C., McKnight, T. D. and Williams, B. G. (1984) "A Simplified and Efficient Vector-Primer cDNA Cloning System". In press in *Gene*.
2. Barton, K. A., Binns, A. N., Matzke, A. J. M. and Chilton, M.-D., Cell, 32:1033-1043 (1983).
3. Bevan, M. W. and Chilton, M. -D., *Annu. Rev. Genet.*, 6:357-384 (1982).
4. Bevan, M., Barnes, W. M. and Chilton, M.-D., *Nucleic Acids Res.*, 11:369-385 (1983).
5. Bomhoff, G., Klapwijk, P. M., Kester, H. C. M., Schilperoort, R. A., Hernalsteens, J. P. and Schell, J., *Mol. Gen. Genet.* 145:177-181 (1976).
6. Boyer, H. W. and Roulland-Dussoix, D., *J. Mol. Biol.*, 41:459-472 (1969).
7. DeCleene, M. and DeLey, J., *Bot. Rev.*, 42:389-466 (1976).
8. deFramond, A. J., Barton, K. A. and Chilton, M.-D., *Biotech.*, April, 1983, pp. 262-269.
9. DeGreve, H., Leemans, J., Hernalsteens, J. P., Thia-Toong, L., DeBueckeleer, M., Willmitzer, L., Otten, L., VanMontagu, M., and Schell, J., *Nature* 300:752-755 (1982).
10. Depicker, A., Stachel, S., Dhaese, P., Zambryski, P. and Goodman, H. M., *J. Mol. Appl. Genet.*, 1:561-573 (1982).
11. Ditta, G., Stanfield, S., Corbin, D. and Helinski, D. R., *Proc. Natl. Acad. Sci. USA*, 77:7347-7351 (1980).
12. Garfinkel, D. J. and Nester, E. W., *J. Bacteriol.*, 144:731-743 (1980).
13. Garfinkel, D. J., Simpson, R. B., Ream, L. W., White, F. F., Gordon, M. P. and Nester, E. W., *Cell*, 27:143-153 (1981).
14. Hoekema, A., Hirsch, P. R., Hooykaas, P. J. J. and Schilperoort, R. A., *Nature*, (Lond.) 303:179-180 (1983a).
15. Hoekema, A., van Haaren, M. J. J., Hille, J., Hoge, J. H. C., Hooykaas, P. J., Krens, F. A., Wullums, G. J. and Schilperoort, R. A., "*Agrobacterium tumefaciens* and its Ti-plasmid as Tools in Transformation of Plant Cells" in *Plant Molecular Biology*, A. R. Liss, Inc., New York (1983b), at pp. 2-22.
16. Hoekema, A., Hooykaas, P. J., and Schilperoort, R. A., *J. Bacteriol.*, 158:383-385 (1984).
17. Holsters, M., de Waele, D., Depicker, A., Messens, E., van Montagu, M. and Schell, J., *Mol. Gen. Genet.*, 163:181-187 (1978).
18. Joos, H., Inze, D., Kaplan, A., Sormann, M., VanMontagu, M., and Schell, J., *Cell*, 32:1057-1067 (1983).
19. Leemans, J., Shaw, Ch., Deblaere, R., DeGreve, H., Hernalsteens, J. P., Maes, M., Van Montagu, M. and Schell, J., *J. Mol. Appl. Genet.*, 1:149-164 (1981).
20. Lippincott, B. B. and Lippincott, J. A., *J. Bacteriol.*, 97:620-628 (1969).
21. Maniatis, T., Fritsch, E. F. and Sambrook, J., *Molecular Cloning, A Laboratory Manual*, Cold Spring Harbor Laboratory, (1982).
22. Ooms, et al., *Plasmid* 7:15-29 (1982).
23. Ooms, G., Hooykaus, P. J. J., Moolenaar, G. and Schilperoort, R. A., *Gene* 14:33-50 (1981).
24. Ooms, G., Karp, A. and Roberts, J., *Theor. Appl. Genet.*, 66:169-172 (1983).
25. Ooms, G., Klapwijk, Poulis, J. A. and Schilperoort, R. A., *J. Bacteriol.*, 144:82-91 (1980).
26. Otten, L. A. B. M. and Schilperoort, R. A., *Biochim. Biophys. Acta*, 527:497-500 (1978).
27. Otten, L., DeGreve, H., Hernalsteens, J. P., VanMontagu, M., Schneider, O., Straub, J., Schell, J., *Mol. Gen. Genet.*, 183:209-213 (1981).
28. Schell, J., and Van Montagu, M., *Biotech.*, April, 1983, pp. 175-180.
29. Simpson, R. B., Lillis, M., Margossian, L. and McKnight, T. D., "DNA Transfer to Plant Cells Using the Ti Plasmid Vector" in *Plant Molecular Biology*, R. Liss, Inc., New York, N.Y. (1983) at pp. 23-34.
30. Southern, E. M., *J. Mol. Biol.*, 98:503-517 (1975).
31. Thomashow, M. F., Nutter, R., Montoya, A. L., Gordon, M. P. and Nester, E. W., *Cell*, 19:729-739 (1980).
32. Vieira, J. and Messing, J., *Gene*, 19:259-268 (1982).
33. White, F. F., Ghidossi, G., Gordon, M. P. and Nester, E. W., *Proc. Natl. Acad. Sci. USA*, 79:3193-3197 (1982).
34. Willmitzer, L., Dhaese, P., Schreier, P. H., Schmalenbach, W., van Montagu, M. and Schell, J., *Cell*, 32:1045-1056 (1983).
35. Yadav, N. S., Vanderleyden, J., Bennett, D. R., Barnes, W. M. and Chilton, M.-D., *Proc. Natl. Acad. Sci. USA*, 79:6322-6326 (1982).
36. Yang, F. and Simpson, R. B., *Proc. Nat. Acad. Sci. USA* 78:4151-4155 (1981).
37. Zambryski, P., Depicker, A., Kruger, K. and Goodman, H. M., *J. Mol. Appl. Genet.*, 1:361-370 (1982).
38. Zambryski, P., Holsters, M., Kruger, K., Depicker, A., Schell, J., Van Montagu, M. and Goodman, H. M., *Science*, 209:1385-1391 (1980).

SUMMARY

Thus it can be seen that the present invention discloses a useful in vivo method for transforming and regenerating whole plants. Plants transformed and regenerated by the method of the invention contain cells having heterologous DNA integrated into their genomes but do not contain any oncogenes, even disabled ones. Such transformed plants are fertile and can transmit heterologous DNA to their progeny following sexual reproduction.

Various modifications of the invention, in addition to those shown and described herein will become apparent to those skilled in the art from the foregoing description and accompanying drawings. Such modifications are intended to fall within the scope of the appended claims.

What is claimed is:

1. An in vivo method for transforming and regenerating whole dicotyledenous plants comprising:
   (a) infecting a dicotyledenous plant (P) with Rhizobiaceae bacteria containing
      (1) virulence functions,
      (2) a first plasmid containing T-DNA terminal sequences flanking oncogenic factors capable of inducing a shoot-bearing shooty tumor on plant (P), and
      (3) a second plasmid containing T-DNA terminal sequences flanking heterologous transfer DNA capable of being integrated into nuclear DNA of plant (P) cells wherein said second plasmid does not contain any oncogenic factors;
   (b) maintaining said infected dicotyledenous plant (P) until shoot-bearing shooty tumor develops on said dicotyledenous plant (P);
   (c) selecting those shoots, or progeny thereof wherein said progeny are selected from the group consisting of seeds or tubers, that contain transformed cells having heterologous transfer DNA but not any tumorous DNA integrated into their genomes;
   (d) utilizing said selected shoots, or progeny thereof, to produce whole plants that contain cells having heterologous transfer DNA integrated into their genomes.

2. A method according to claim 1 wherein said shoots, or progeny thereof, are selected as the result of an analysis that demonstrates the presence therein of a gene product coded for by heterologous transfer DNA (h/T-DNA).

3. A method according to claim 2 wherein said selected shoots are allowed to flower, self-pollinate and produce $F_1$ seeds without being removed from said shooty tumor.

4. A method according to claim 2 wherein progeny from said shoots are produced by removing said shoots from said shooty tumor, then rooting said removed shoots in a suitable rooting medium before allowing said shoots to flower, self-pollinate and produce $F_1$ seeds.

5. A method according to claim 1 wherein said dicotyledenous plant (P) is any dicotyledenous plant capable of forming a shoot-bearing shooty tumor following infection with an *Agrobacterium tumefaciens* shooty mutant strain.

6. A method according to claim 1 wherein said dicotyledenous plant (P) is infected by allowing said Rhizobiaceae bacteria from step (a) to enter said dicotyledenous plant at a wound site.

7. A method according to claim 1, subsection (a) (1), wherein said virulence functions are virulence functions from *Agrobacterium tumefaciens* tumor inducing (Ti) plasmids.

8. A method according to claim 1, subsection (a) (1), wherein said virulence functions are virulence functions from *Agrobacterium rhizogenes* root inducing (Ri) plasmids.

9. A method according to claim 1, subsection (a) (2), wherein said oncogenic factors are oncogenic factors from *Agrobacteria tumefaciens* tumor inducing (Ti) plasmids having mutations at the tms locus.

10. A method according to claim 9 wherein said Ti plasmids having mutations at the tms locus are nopaline-type Ti plasmids.

11. A method according to claim 9 wherein said Ti plasmids having mutations at the tms locus are octopine-type Ti plasmids.

12. A method according to claim 1 wherein said Rhizobiaceae are of a "mixed infection" type composed of (a) a first Agrobacterium strain containing plasmids having virulence functions and oncogenic factors and, (b) a second Agrobacterium strain containing: (1) a first plasmid having heterologous transfer DNA capable of being integrated into the nuclear genome of dicotyledenous plant (P) cells wherein said first plasmid does not contain any oncogenic factors, and (2) a separate second plasmid having virulence functions and non-operative oncogenic factors.

13. A method according to claim 1 wherein said Rhizobiaceae bacteria are of a "single infection" type composed of a single strain of Rhizobiaceae bacteria containing (1) said virulence functions, (2) said first plasmid containing said oncogenic factors and (3) said second plasmid containing said heterologous transfer DNA but not any oncogenic factors.

14. A method according to claim 1, subsection (a) (3), wherein said second plasmid also contains a broad-host-range replicon.

15. A method according to claim 14 wherein said heterologous DNA is from about 1 to about 50,000 base pairs in length.

16. A method according to claim 15 wherein said heterologous DNA codes for at least two genes.

17. A method according to claim 1, subsection (a) (3), wherein said second plasmid is selected from the group consisting of pARC2 and pARC4.

18. A method according to claim 1 wherein said infected dicotyledenous plant (P) is maintained in a greenhouse under controlled environmental conditions until a shoot-bearing shooty tumor develops at or near the infection site.

19. A method according to claim 1 wherein said selected shoots are allowed to flower, self-pollinate and produce $F_1$ seeds from which $F_1$ seedlings are obtained after said $F_1$ seeds are set and allowed to germinate.

20. A method according to claim 1 wherein said shoots, or seed progeny thereof, that contain cells having h/T-DNA but not any tumorous DNA integrated into their nuclear genomes, are propagated by means of sexual reproduction.

21. A method according to claim 1 wherein said virulence functions, described in claim 1 subsection (a) (1), are carried on said first plasmid described in claim 39 subsection (a) (2).

22. A method according to claim 1 wherein said virulence functions, described in claim 1 subsection (a) (1), are carried on a third plasmid that is separate and distinct from either said first or second plasmids.

23. An in vivo method for transforming and regenerating whole dicotyledenous plants comprising
   (a) selecting a tumor-inducing (Ti) plasmid-bearing virulent *Agrobacterium tumefaciens* strain capable of forming shoot-bearing shooty tumors on dicotyledenous plant (P);
   (b) wounding said dicotyledenous plant (P) and infecting the wound site with: (1) a tumor-inducing (Ti) plasmid bearing virulent *Agrobacterium tumefaciens* strain capable of forming shoot-bearing shooty tumors on plant (P), and (2) a second plasmid containing T-DNA terminal sequences flanking heterologous transfer DNA capable of being integrated into nuclear DNA of plant (P) cells wherein said second plasmid does not contain any oncogenic factors;

(c) maintaining said infected dicotyledenous plant (P) until shoots develop at or near the wound site;

(d) selecting those shoots, or progeny thereof wherein said progeny are selected from the group consisting of seeds or tubers, that contain transformed cells having heterologous transfer DNA but not any tumorous DNA integrated into their genomes;

(e) utilizing said selected shoots, or progeny thereof, to produce whole dicotyledenous plants that contain cells having heterologous transfer DNA integrated into their genomes.

24. A plant transformed and regenerated according to the methods as claimed in any one of claims 1-13.

25. Seeds containing h/T-DNA but not any tumorous DNA from plants transformed and regenerated according to the methods as claimed in any one of claims 1-13.

26. Carrier vector pARC2.

27. Carrier vector pARC4.

* * * * *